(12) United States Patent
Curra et al.

(10) Patent No.: US 8,900,145 B2
(45) Date of Patent: Dec. 2, 2014

(54) ULTRASOUND SYSTEMS AND METHODS FOR REAL-TIME NONINVASIVE SPATIAL TEMPERATURE ESTIMATION

(75) Inventors: Francesco P. Curra, Brier, WA (US); Neil R. Owen, Bothell, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 74 days.

(21) Appl. No.: 13/418,203

(22) Filed: Mar. 12, 2012

(65) Prior Publication Data

US 2012/0232388 A1 Sep. 13, 2012

Related U.S. Application Data

(60) Provisional application No. 61/451,451, filed on Mar. 10, 2011.

(51) Int. Cl.
*A61B 8/00* (2006.01)
*A61B 8/08* (2006.01)
*A61N 7/02* (2006.01)
*A61B 19/00* (2006.01)
*A61B 18/00* (2006.01)

(52) U.S. Cl.
CPC ....... *A61B 8/5223* (2013.01); *A61B 2019/5276* (2013.01); *A61B 2018/00791* (2013.01); *A61B 8/485* (2013.01); *A61B 8/587* (2013.01); *A61N 7/02* (2013.01); *A61B 8/466* (2013.01)
USPC ........... 600/438; 600/439; 600/447; 600/458; 601/2; 601/3

(58) Field of Classification Search
USPC .................. 600/437, 438, 439, 447; 601/2, 3
See application file for complete search history.

(56) References Cited

U.S. PATENT DOCUMENTS

| | | | |
|---|---|---|---|
| 6,050,947 A * | 4/2000 | Rhyne et al. | 600/447 |
| 2003/0018256 A1* | 1/2003 | Sasaki et al. | 600/439 |
| 2004/0102703 A1* | 5/2004 | Behren et al. | 600/443 |
| 2006/0052699 A1* | 3/2006 | Angelsen et al. | 600/437 |
| 2007/0106157 A1* | 5/2007 | Kaczkowski et al. | 600/438 |
| 2008/0177180 A1* | 7/2008 | Azhari et al. | 600/439 |
| 2008/0195003 A1* | 8/2008 | Sliwa et al. | 601/3 |
| 2009/0178483 A1* | 7/2009 | Angelsen et al. | 73/597 |
| 2010/0036244 A1* | 2/2010 | Angelsen et al. | 600/438 |
| 2010/0036292 A1* | 2/2010 | Darlington et al. | 601/2 |
| 2011/0087096 A1* | 4/2011 | Behar | 600/438 |
| 2011/0251524 A1* | 10/2011 | Azhari et al. | 601/2 |

OTHER PUBLICATIONS

Schroeder W, Martin K, Lorensen W. The Visualization Toolkit—An Object-Oriented Approach to 3D Graphics. Prentice Hall, Upper Saddle River, NJ, 1996.

(Continued)

*Primary Examiner* — Baisakhi Roy
(74) *Attorney, Agent, or Firm* — Perkins Coie LLP

(57) ABSTRACT

Ultrasound systems and methods for real-time noninvasive spatial temperature estimation are disclosed herein. A method for noninvasive temperature estimation in accordance with an embodiment of the present technology can include, for example, propagating ultrasound waves into tissue and detecting echoes of the ultrasound waves. The ultrasound waves can become nonlinear as they propagate into the tissue. The method can further include monitoring changes in tissue temperature in real-time using a spectral-based temperature estimation approach, which correlates nonlinear acoustic effects with changes in tissue temperature.

13 Claims, 7 Drawing Sheets

(4 of 7 Drawing Sheet(s) Filed in Color)

(56) References Cited

OTHER PUBLICATIONS

W. L. Lin, C. T. Liauh, J. Y. Yen, Y. Y. Chen, and M. J. Shieh., "Treatable domain and optimal frequency for brain tumors during ultrasound hyperthermia," Int J Radiat Oncol Biol Phys. 46(1), 239-47 (2000).

L. Mencaglia, R. Guidetti, D. Tonellotto, and A. Fanfani, "Energy focused ultrasound for the clinical treatment of uterine myoma," Ultrasound Med. Biol. 26(2), A207 (2000).

T. Uchida, N. T. Sanghvi, T. A. Gardner, M. O. Koch, D. Ishii, S. Minei, T. Satoh, T. Hyodo, A. Irie, and S. Baba, "Transrectal high-intensity focused ultrasound for treatment of patients with stage T1b-2n0m0 localized prostate cancer: a preliminary report," Urology 59(3), 394-398 (2002).

F. Wu, Z.-B. Wang, W.-Z. Chen, and J.-Z. Zou, "Extracorporeal high intensity focused ultrasound for treatment of solid carcinomas: four-year Chinese clinical experience," Proc. 2nd International Symposium on Therapeutic Ultrasound (Seattle, USA, 2002).

K. Hynynen, A. H. Chung, V. Colucci, and F. A. Jolesz "Potential adverse effects of high-intensity focused ultrasound exposure on blood vessels in vivo," Ultrasound Med Biol 22(2), 193-201 (1996).

S. Vaezy, R. Martin, G. Keilman, P. Kaczkowski, E. Chi, E. Yazaji, M. Caps, S. Poliachik, S. Carter, S. Sharar, C. Cornejo, and L. Crum, "Control of splenic bleeding by using high intensity ultrasound," J Trauma 47(3), 521-5 (1999).

M. L. Denbow, I. H. Rivens, I. J. Rowland, M. O. Leach, N. M. Fisk, and G. R. ter Haar, "Preclinical development of noninvasive vascular occlusion with focused ultrasonic surgery for fetal therapy," Am J Obstet Gynecol 182(2), 387-92 (2000).

K. Hynynen, V. Colucci, A. Chung, and F. Jolesz "Noninvasive arterial occlusion using MRIguided focused ultrasound," Ultrasound Med Biol 22, 1071-1077 (1996).

C. Chaussy, S. Thuroff, F. Lacoste, and A. Gelet, "HIFU and Prostate Cancer: The European Experience," Proc. 2nd Internationa I Symposium on Therapeutic Ultrasound (Seattle, USA, 2002).

T. Uchida, N. T. Sanghvi, and T. A. Gardner, "High-intensity focused ultrasound (HIFU) for localized prostate cancer treatment," Proc. 2nd International Symposium on Therapeutic Ultrasound (Seattle, USA, 2002) (in press).

Cline HE, Schenck JF, Watkins RD, Hynynen K, Jolesz FA. Magnetic resonance-guided thermal surgery. Magn Reson Med 1993; 30: 98-106.

Cline HE, Hynynen K, Hardy CJ, Watkins RD, Schenck JF, Jolesz FA. MR temperature mapping of focused ultrasound surgery. Magn Reson Med 1994; 31: 628-636.

Hynynen K, Darkazanli A, Damianou CA, Unger E, Schenck JF. Tissue thermometry during ultrasound exposure. Eur Urol 1993; 23 Suppl 1: 12-16.

Cline HE, Hynynen K, Schneider E, Hardy CJ, Maier SE, Watkins RD, Jolesz FA. Simultaneous magnetic resonance phase and magnitude temperature maps in muscle. Magn Reson Med 1996; 35: 309-315.

Bohris C, Schreiber WG, Jenne J, Simiantonakis I, Rastert R, Zabel HJ, Huber P, Bader R, Brix G. Quantitative MR temperature monitoring of high-intensity focused ultrasound therapy. Magn Reson Imaging 1999; 17: 603-610.

Kuroda K, Chung AH, Hynynen K, Jolesz FA. Calibration of water proton chemical shift with temperature for noninvasive temperature imaging during focused ultrasound surgery. J Magn Reson Imaging 1998; 8: 175-181.

Bohris C, Jenne JW, Rastert R, Simiantonakis I, Brix G, Spoo J, Hlavac M, Nemeth R, Huber PE, Debus J. MR monitoring of focused ultrasound surgery in a breast tissue model in vivo. Magn Reson Imaging 2001; 19: 167-175.

Hynynen K, McDannold N, Mulkern RV, Jolesz FA. Temperature monitoring in fat with MRI. Magn Reson Med 2000; 43: 901-.

Cline HE, Schenck JF, Hynynen K, Watkins RD, Souza SP, Jolesz FA. MR-guided focused ultrasound surgery. J Comput Assist Tomogr 1992; 16: 956-965.

Hynynen K, Darkazanli A, Unger E, Schenck JF. MRI-guided noninvasive ultrasound surgery. Med Phys 1993; 20: 107-115.

Hynynen K, Darkazanli A, Damianou CA, Unger E, Schenck JF. The usefulness of a contrast agent and gradient-recalled acquisition in a steady-state imaging sequence for magnetic resonance imaging-guided noninvasive ultrasound surgery. Invest Radiol 1994; 29: 897-903.

Rouviere O, Lyonnet D, Raudrant A, Colin-Pangaud C, Chapelon JY, Bouvier R, Dubernard JM, Gelet A. MRI appearance of prostate following transrectal HIFU ablation of localized cancer. Eur Urol 2001; 40: 265-274.

Rowland IJ, Rivens I, Chen L, Lebozer CH, Collins DJ, ter Haar GR, Leach MO. MRI study of hepatic tumours following high intensity focused ultrasound surgery. Br J Radiol 1997; 70: 144-153.

Wu T, Felmlee JP, Greenleaf JF, Riederer SJ, Ehman RL. Assessment of thermal tissue ablation with MR elastography. Magn Reson Med 2001; 45: 80-87.

Wu T, Felmlee JP, Greenleaf JF, Riederer SJ, Ehman RL. MR imaging of shear waves generated by focused ultrasound. Magn Reson Med 2000; 43: 111-115.

Hynynen K, Pomeroy O, Smith DN, Huber PE, McDannold NJ, Kettenbach J, Baum J, Singer S, Jolesz FA. MR imaging-guided focused ultrasound surgery of fibroadenomas in the breast: a feasibility study. Radiology 2001; 219: 176-185.

Hardy CJ, Cline HE, Watkins RD. One-dimensional NMR thermal mapping of focused ultrasound surgery. J Comput Assist Tomogr 1994; 18: 476-483.

Fjield T, Fan X, Hynynen K. A parametric study of the concentric-ring transducer design for MRI guided ultrasound surgery. J Acoust Soc Am 1996; 100: 1220-1230.

Hynynen K, Freund WR, Cline HE, Chung AH, Watkins RE, Vetro JP, Jolesz FA. A clinical, noninvasive, MR imaging-monitored ultrasound surgery method. Radiographics 1996; 16: 185-195.

Jolesz FA, Blumenfeld SM. Interventional use of magnetic resonance imaging. Magn Reson Q 1994; 10: 85-96.

Jolesz FA, Hynynen K. Magnetic resonance image-guided focused ultrasound surgery. Cancer J 2002; 8 Suppl 1: S100-112.

Bush NL, Rivens I, ter Haar GR, Bamber JC. Acoustic properties of lesions generated with an ultrasound therapy system. Ultrasound Med Biol 1993; 19: 789-801.

Yang R, Sanghvi NT, Rescorla FJ, Galliani CA, Fry FJ, Griffith SL, Grosfeld JL. Extracorporeal liver ablation using sonography-guided high-intensity focused ultrasound. Invest Radiol 1992; 27: 796-803.

Vaughan MG, ter Haar GR, Hill CR, Clarke RL, Hopewell JW. Minimally invasive cancer surgery using focused ultrasound: a preclinical, normal tissue study. Br J Radiol 1994; 67: 267-274.

Prat F, Centarti M, Sibille A, Abou el Fadil FA, Henry L, Chapelon JY, Cathignol D. Extracorporeal high-intensity focused ultrasound for VX2 liver tumors in the rabbit. Hepatology 1995; 21: 832-836.

ter Haar G, Sinnett D, Rivens I. High intensity focused ultrasound—a surgical technique for the treatment of discrete liver tumours. Phys Med Biol 1989; 34: 1743-1750.

Wang Z, Li F, Bai J, Wu F, Zou J, Du Y, Chen W. Study on energy efficiency factor of ultrasound therapy. In: Andrew MA, Crum LA, Vaezy S (eds.), Proceedings of the 2nd Internat'l Symposium on Therapeutic Ultrasound, Seattle, WA, Jul. 29-Aug. 1, 2002. American Institute of Physics Press/Univ. Washington, 2003, pp. 112-119.

Seip RE, Ebbini ES. Noninvasive estimation of tissue temperature response to heating fields using diagnostic ultrasound. IEEE Trans Biomed Eng 1995; 42: 828-839.

Miller NR, Bamber JC, Meaney PM. Fundamental limitations of noninvasive temperature imaging by means of ultrasound echo strain estimation. Ultrasound Med Biol 2002; 28: 1319-1333.

Righetti R, Kallel F, Stafford RJ, Price RE, Krouskop TA, Hazle JD, Ophir J. Elastographic characterization of HIFU-induced lesions in canine livers. Ultrasound Med Biol 1999; 25: 1099-1113.

Konofagou E, Thierman J, Hynynen K. A focused ultrasound method for simultaneous diagnostic and therapeutic applications—a simulation study. Phys Med Biol 2001; 46: 2967-2984.

Konofagou EE, Thierman J, Karjalainen T, Hynynen K. The temperature dependence of ultrasound stimulated acoustic emission. Ultrasound Med Biol 2002; 28: 331-338.

(56) References Cited

OTHER PUBLICATIONS

Ribault M, Chapelon JY, Cathignol D, Gelet A. Differential attenuation imaging for the characterization of high intensity focused ultrasound lesions. Ultrason Imaging 1998; 20: 160-177.
Nightingale K, Bentley R, Trahey G. Observations of tissue response to acoustic radiation force: opportunities for imaging. Ultrason Imaging 2002; 24: 129-138.
Anand A, Kaczkowski PJ. Monitoring formation of high intensity focused ultrasound (HIFU) induced lesions using backscattered ultrasound. Acoustics Research Letters Online 2004; 5: 88-94.
Anand A, Kaczkowski PJ. A model-based noninvasive temperature estimation technique for monitoring HIFU therapy using backscattered ultrasound. J Acoust Soc Am 2004; 115.
Anand A, Kaczkowski PJ. Non-invasive measurement of in situ thermal diffusivity and local heat source using backscattered ultrasound for thermal therapy planning and monitoring. IEEE Symposium on Ultrasonics 2004: (in press).
Clarke RL, ter Haar GR. Production of harmonics in vitro by high-intensity focused ultrasound. Ultrasound Med Biol 1999; 25: 1417-1424.
Swindell W. A theoretical study of nonlinear effects with focused ultrasound in tissues: an "acoustic bragg peak". Ultrasound Med Biol 1985; 11: 121-130.
Curra FP. Medical Ultrasound Algorithm for Noninvasive High Intensity Ultrasound Applications. Ph.D thesis, 2001, Univ Washington: Seattle, WA.
Fry FJ, Dines KA, Reilly CR, Goss SA. Losses in tissue associated with finite amplitude ultrasound transmission. Ultrasound Med Biol 1989; 15: 481-497.
Fry FJ, Reilly CR, Dines KA, Etchison MA, Trauner EJ. Absorption in liver at the focus of an ultrasonic shock wave field. Ultrasound Med Biol 1991; 17: 65-69.
Damianou CA, Sanghvi NT, Fry FJ, Maass-Moreno R. Dependence of ultrasonic attenuation and absorption in dog soft tissues on temperature and thermal dose. J Acoust Soc Am 1997; 102: 628-634.
Bloch S. Ultrasound tissue characterization: towards high-intensity focused ultrasound treatment monitoring. In: BioEngineering. 1997, University of Washington: Seattle.
Bush NL, Riven I, ter Haar GR, Bamber JC. Acoustic properties of lesions generated with an ultrasound therapy system. Ultrasound Med Biol 1993;19:789-801.
Clarke RL, ter Haar GR. Temperature rise recorded during lesion formation by high-intensity focused ultrasound. Ultrasound Med Biol 1997; 23: 299-306.
Brentnall, MD, Martin RW, Vaezy S, Kaczkowski P, et al., "A new HIFU applicator for surgical applications", IEEE Trans Ultra Ferro Freq Contr; 48:53-63, 2001.
Kaczkowski PJ, Keilman GW, Cunitz BW, Martin RW, Vaezy S, and Crum LA, "High Intensity Focused Ultrasound (HIFU) array system for Image-guided ablative therapy (IGAT)," SPIE Photonics West, BIOS 2003, 2003.
Anand A, Kaczkowski PJ, Daigle R, Huang L, Paun M, Beach KW, Crum LA. Using the ATL HDI 1000 to collect demodulated RF data for monitoring HIFU lesion formation. In: M.F.I. W.F. Walker (ed.), SPIE Medical imaging. San Diego. SPIE.
Anand A, Kaczkowski P, Daigle R, Crum L. Using the ATL HDI 1000 ultrasound scanner for tissue elasticity imaging. In: J. Ophir (ed.), First International Conference on the Ultrasonic Measurement and Imaging of Tissue Elasticity. Niagara Falls, Ontario, Canada, Oct. 20-23, 2002.
Ophir J, Alam SK, Garra B, Kallel F, Konofagou E, Krouskop T, Varghese T. Elastography: ultrasonic estimation and imaging of the elastic properties of tissues. Proc Inst Mech Eng [H] 1999; 213: 203-233.
Gertner MR, Wilson BC, Sherar MD. Ultrasound properties of liver tissue during heating. Ultrasound Med Biol 1997; 23: 1395-1403.
Worthington AE, Sherar MD. Changes in ultrasound properties of porcine kidney tissue during heating. Ultrasound Med Biol 2001; 27: 673-682.
Worthington AE, Trachtenberg J, Sherar MD. Ultrasound properties of human prostate tissue during heating. Ultrasound Med Biol 2002; 28: 1311-1318.

Leotta DF, Primozich JF, Beach KW, Bergelin RO, Strandness DE Jr. Serial measurement of crosssectional area in peripheral vein grafts using three-dimensional ultrasound. Ultrasound Med Biol, 27:61-68, 2001a.
Leotta DF, Paun M, Beach KW, Kohler TR, Zierler RE, Strandness DE Jr. Measurement of abdominal aortic aneurysms using three-dimensional ultrasound imaging: preliminary report. J Vasc Surg, 33: 700-707, 2001b.
Leotta DF, Martin RW. Three-dimensional ultrasound imaging of the rotator cuff: spatial compounding and tendon thickness measurement. Ultrasound Med Biol, 26:509-525, 2000.
Leotta DF, Primozich JF, Lowe CM, Karr LN, Bergelin RO, Beach KW, Zierler RE. Measurement of anastomosis geometry in lower extremity bypass grafts with 3D ultrasound imaging. Ultrasound Med Biol, 31:1305-1315, 2005a.
Leotta DF, Primozich JF, Henderson SM, Karr LN, Bergelin RO, Beach KW, Zierler RE. Display of spatially-registered Doppler spectral waveforms and three-dimensional vein graft geometry. Ultrasound Med Biol, 31:1317-1326, 2005b.
Boorsboom JMG, Chin CT, Bouakaz A, Versluis M, de Jong N. Harmonic chirp imaging method for ultrasound contrast agent. IEEE Trans Ultra Ferro Freq Contr; 52:241-249, 2005.
Curra FP, Mourad PD, Khokhlova VA, Cleveland RO, Crum LA, "Numerical simulations of heating patterns and tissue temperature response due to high-intensity focused ultrasound", IEEE Trans Ultra Ferro Freq Contr; 47:1077-89, 2000.
Curra FP, Kargl SG, Crum LA, "Parameter space investigation for optimal thermal lesion generation in noninvasive HIFU application", in Therapeutic Ultrasound, Proceedings of the 2nd International Symposium, Andrew MA, Crum LA, Vaezy S (Eds), American Institute of Physics Press, 275-281, 2002.
Curra FP, Kargl SG, Crum LA, "Fast, dynamically adaptive algorithm for nonlinear acoustics and HIFU modeling in biological media", in Proceedings of the 18th International Congress on Acoustics, 17-20, 2004.
Bloch SH, Bailey MR, Crum LA, Kaczkowski PJ. Measurements of sound speed in excised tissue over temperatures expected under high-intensity focused ultrasound conditions. J Acoust Soc Am 1998; 103.
Swelden, W., "The Lifting Scheme: A construction of second-generation wavelets", SIAM J. Math. Anal., 29(2), 511-546, 1998.
Pernot M, Tanter M, Berco J, Waters KR, Fink M. Temperature estimation using ultrasonic spatial compound imaging. IEEE Trans UFFC 2004; 51: 606-615.
Chen W-S, Lafon C, Matula TJ, Vaezy S, Brayman AA, Crum LA. Mechanism of lesion formation in high intensity ultrasound therapy. In: Andrew MA, Crum LA, Vaezy S (eds.), Proceedings of the 2nd Internat'l Symposium on Therapeutic Ultrasound, Seattle, WA, Jul. 29-Aug. 1, 2002. American Institute of Physics Press/Univ. Washington, 2003, pp. 400-409.
Fessenden P, Lee ER, Samulski TV. Direct temperature measurement. Cancer Res. Oct. 1984; 44(10 Suppl):4799s-4804s.
Horder MM, Barnett SB, Vella GJ, Edwards MJ, Wood AK. In vivo heating of the guinea-pig fetal brain by pulsed ultrasound and estimates of thermal index. Ultrasound Med Biol. Nov. 1998; 24(9):1467-74.
McDannold N, King RL, Hynynen K. MRI monitoring of heating produced by ultrasound absorption in the skull: in vivo study in pigs. Magn Reson Med. May 2004 ;51(5):1061-5.
Erez A, Shitzer A. Controlled destruction and temperature distributions in biological tissues subjected to monoactive electrocoagulation. J Biomech Eng. Feb. 1980;102(1):42-9.
Leotta DF. An efficient calibration method for freehand 3-D ultrasound imaging systems. Ultrasound Med Biol, 30:999-1008, 2004.
Leotta DF, Detmer PR, Martin RW. Performance of a miniature magnetic sensor for three-dimensional ultrasound imaging. Ultrasound Med Biol, 23:597-609, 1997a.
Leotta DF, Munt B, Bolson EL, Martin RW, Kraft C, Otto CM, Sheehan FH. Quantitative three-dimensional echocardiography by rapid imaging from multiple transthoracic windows: in vitro validation and initial in vivo studies. J Am Soc Echocardiography, 10:830-839, 1997b.

\* cited by examiner

ULTRASOUND SYSTEMS AND METHODS FOR REAL-TIME NONINVASIVE SPATIAL TEMPERATURE ESTIMATION

CROSS-REFERENCE TO RELATED APPLICATION(S)

This application claims the benefit of pending U.S. Provisional Patent Application No. 61/451,451, filed Mar. 10, 2011, entitled "ULTRASOUND SYSTEMS AND METHODS FOR REAL-TIME NONINVASIVE SPATIAL TEMPERATURE ESTIMATION," which is incorporated herein by reference in its entirety.

STATEMENT REGARDING FEDERALLY SPONSORED RESEARCH

This invention was made with government support under grant R01DK075090-01A1, awarded by the National Institutes of Health. The government has certain rights in the invention.

TECHNICAL FIELD

The present technology relates generally to ultrasound systems. In particular, several embodiments are directed to ultrasound systems and methods for real-time noninvasive spatial temperature estimation.

BACKGROUND

Various minimally invasive and noninvasive medical procedures use targeted applications of energy to increase the temperature of tissue and form heat-induced lesions at a treatment site in the tissue. High-intensity focused ultrasound ("HIFU") waves, for example, can be propagated into tissue toward a discrete focal region, and the accumulation of the resultant harmonic frequencies can induce rapid heating at the focal region that ablates, necrotizes, and/or otherwise damages the tissue. In a clinical setting, HIFU-induced heating can be used to treat benign and malignant tumors (e.g., in the brain, uterus, prostate, liver, etc.) and/or occlude blood vessels (e.g., to induce hemostasis of internal bleeds, intervene in fetal blood sharing anomalies, and confine tumor blood supply). During HIFU therapy and/or other treatments that form heat-induced lesions, image guidance and treatment monitoring (e.g., temperature monitoring) can be used for controlling and optimizing the parameters of the treatment and assessing its efficacy.

HIFU therapies are typically used with magnetic resonance imaging ("MRI") to monitor tissue temperature and/or provide image guidance. For example, MRI can be used to map a temperature profile of a treatment site with a relatively high spatial resolution (e.g., approximately to 2 mm$^2$), determine treatment volumes (e.g., magnetic resonance images indicate coagulated tissue size and location above a threshold thermal dose), provide post-treatment verification, and follow post-treatment tissue repair. Although MRI has relatively good spatial and temperature resolutions, MRI has a limited time resolution that is inadequate for motion compensation during therapies and causes misregistration. In addition, MRI cannot estimate temperatures above approximately 65° C. (when tissues begin to denature and proton relaxation becomes dominant), therefore making it unsuitable for HIFU therapies that induce focal temperatures ranging from approximately 60-90° C. Moreover, the high costs associated with MRI limit its availability to patients and physicians.

Ultrasound-based monitoring methods can also be used for treatment monitoring during HIFU therapies, and can be significantly less expensive than MRI-based methods. Unlike MRI, ultrasound-based monitoring has a relatively high temporal resolution (e.g., tens of Hertz). Some HIFU systems use B-mode ultrasound for treatment monitoring, such as HIFU devices made by Chongqing Haifu Technology, Co. of Barcelona, Spain and the Sonoblate® 500 made by Focus Surgery, Inc. of Indianapolis, Ind. During a HIFU therapy, HIFU-induced bubble formations increase backscatter and produce a hyperechoic region that correlates to the HIFU focal region. B-mode ultrasound can use this hyperechogenicity to help direct therapy and measure tissue coagulation. However, B-mode ultrasound systems cannot use the induced hyperechogenicity to provide a direct indication of tissue temperature or damage. In other types of ultrasound-based monitoring, radiofrequency (RF) signals from diagnostic ultrasound scanners are used to form maps based on temperature-induced changes in tissue resonances. However, RF-based maps are currently limited to temperatures well below the coagulation threshold, and therefore cannot be used during HIFU or other high-temperature therapies. Various other ultrasound-based temperature monitoring techniques have also been explored. For example, elastography-based temperature estimation methods can use raw ultrasound RF data from images obtained before and after external tissue compression to image HIFU lesions based on changes in tissue stiffness. Other elastography-based monitoring systems, such as ultrasound-stimulated acoustic emission methods, map tissue temperature by generating low frequency radiation forces. The radiation forces have amplitudes that depend on tissue stiffness and absorption (i.e., acoustic emissions vary linearly with temperature), but only for temperatures below the coagulation threshold (when then the strain-temperature relationship is abolished). "Before and after" ultrasound RF data has been used to form images based on HIFU-induced changes, and is therefore insensitive to tissue inhomogeneities. These and other ultrasound-based temperature estimation methods (e.g., acoustic radiation force imaging) fail to provide real-time temperature mapping for the temperatures reached during HIFU therapies and other therapies that form heat-induced lesions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The present technology is directed to ultrasound systems and methods for real-time noninvasive spatial temperature estimation. In several embodiments, for example, a method for noninvasively estimating temperature can include transmitting ultrasound waves into tissue using an ultrasound source. The ultrasound waves can become nonlinear at or near a focal region of the ultrasound source, and the ultrasound source can detect the reflected harmonics of the nonlinear ultrasound waves. The method can further include determining the tissue temperature at the focal region in real-time using the changes in the magnitude of the detected harmonics. For example, a greater magnitude of attenuation in a selected harmonic (e.g., the fourth harmonic) correlates to an increase in tissue temperature. In some embodiments, the method can also incorporate temperature estimations based on acoustic travel time to enhance temperature monitoring.

Certain specific details are set forth in the following description and in FIGS. 1-6 to provide a thorough understanding of various embodiments of the technology. For example, embodiments of noninvasive spatial temperature estimation are discussed in relation to HIFU therapies. The present technology, however, may be used to provide real-time temperature estimation for other modalities that use targeted energy to form a heat-induced lesion in tissue, such as RF ablation and laser therapies. Other details describing well-known structures and systems often associated with ultrasound systems and associated devices have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1-6.

Figure 1:
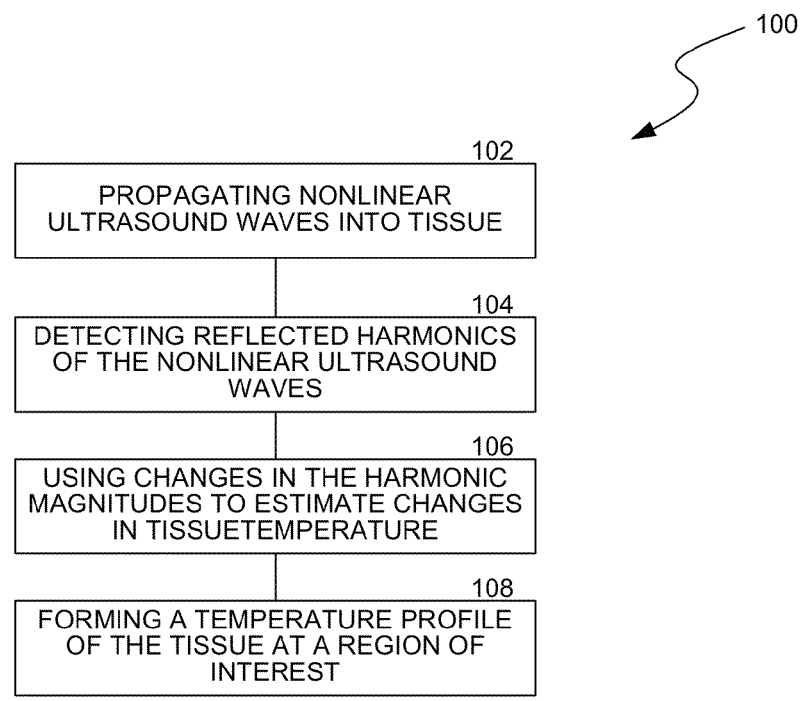
FIG. 1 is a block diagram illustrating a method for real-time spectral-based noninvasive temperature estimation in accordance with an embodiment of the present technology.

FIG. 1 is a block diagram illustrating a method 100 for real-time noninvasive spatial temperature estimation in accordance with an embodiment of the present technology. The method 100 can include launching high energy ultrasound waves into tissue (block 102). The transmitted ultrasound waves can become nonlinear as they propagate through the tissue, and the nonlinear propagation can generate harmonics in the acoustic beam that develop at or near the focal region of the ultrasound transducer from which they are transmitted. At the focal region, the harmonic content can cause acoustic beam narrowing, enhanced tissue heating and proximal focal shifts. The focal region can refer to a point, area, or volume at which the intensity of the ultrasound transducer source is the highest.

The method 100 can further include detecting the harmonic content of the reflected ultrasound waves (block 104). Higher harmonics (e.g., 2nd, 3rd, 4th . . . nth harmonics) generated by the nonlinear waves have enhanced axial and lateral resolution and an enhanced signal-to-noise ratio (e.g., compared to the fundamental frequency). Since nonlinearities develop mainly at or near the focal region of an ultrasound transducer, the nonlinear waves only need to propagate one direction to be detected by the receiving ultrasound transducer (i.e., from the focal region to the ultrasound transducer). This is in contrast to the round-trip propagation path of the original excitation signal (i.e., transmitted away from and reflected back to the ultrasound transducer). Therefore, the attenuation effects (resulting from propagation through a tissue) on the higher harmonics are effectively half those of the high frequency components present in the original driving pulse. Accordingly, the signal provided by the nonlinear ultrasound waves has a frequency rich content that facilitates recording the higher harmonics. As described in greater detail below with reference to FIGS. 4A and 4B, in various embodiments, a single ultrasound source can be configured to both transmit the high energy ultrasound waves and detect the higher harmonics of the reflected waves (i.e., have a broad bandwidth for detecting rich harmonic content).

The nonlinear content of the frequency-rich signal received by the ultrasound transducer can be used to estimate the tissue temperature at or near the focal region (block 106). Without being bound by theory, it is thought that increases in acoustic energy absorption in tissue correspond to increases in tissue temperatures. For example, higher temperatures (e.g., temperatures greater than 50° C.) can have significant effects on tissue attenuation that are thought to be due in large part to an increase in acoustic energy absorption. Higher harmonics are more susceptible to such acoustic energy absorption, and therefore changes in the magnitudes of these higher harmonics between time intervals can be used to indicate changes in temperature. For example, a decrease in the magnitude of a selected harmonic (e.g., a 4th harmonic) within a given time interval indicates an increase in acoustic energy absorption by the tissue (i.e., because more of the harmonic content was absorbed), and therefore a correlated increase in tissue temperature. In other embodiments, changes in the slope between two or more harmonics (e.g., between the 3rd and 4th harmonics, the 3rd and 5th harmonic, etc.) can be correlated to changes in temperature.

Figure 2A:
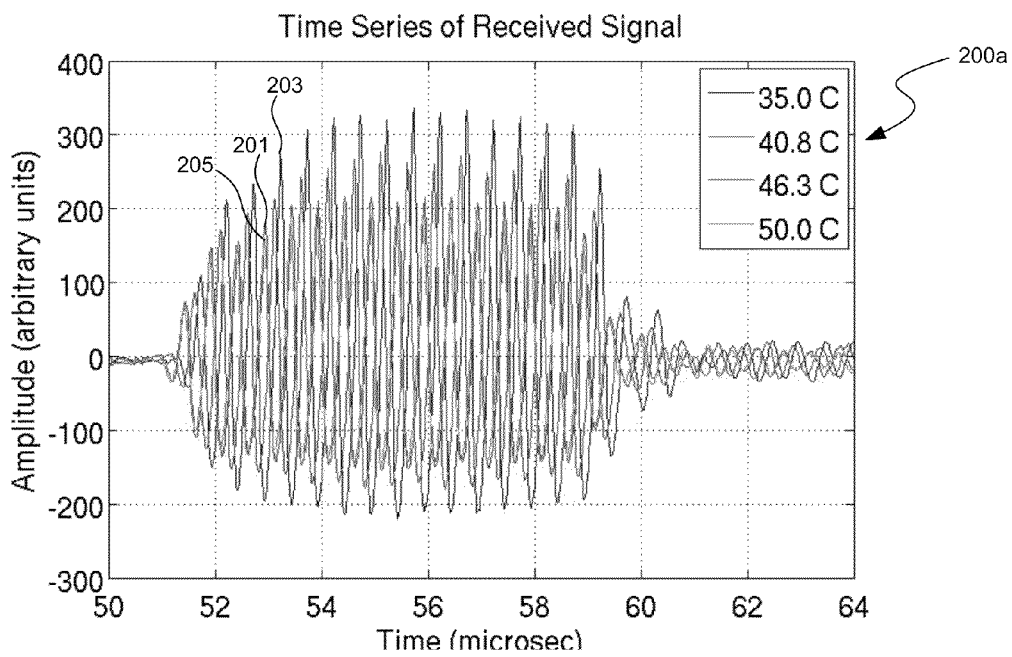
FIG. 2A is a graph illustrating amplitudes of detected ultrasound signals for various different tissue temperatures in accordance with an embodiment of the present technology.
Figure 2B:
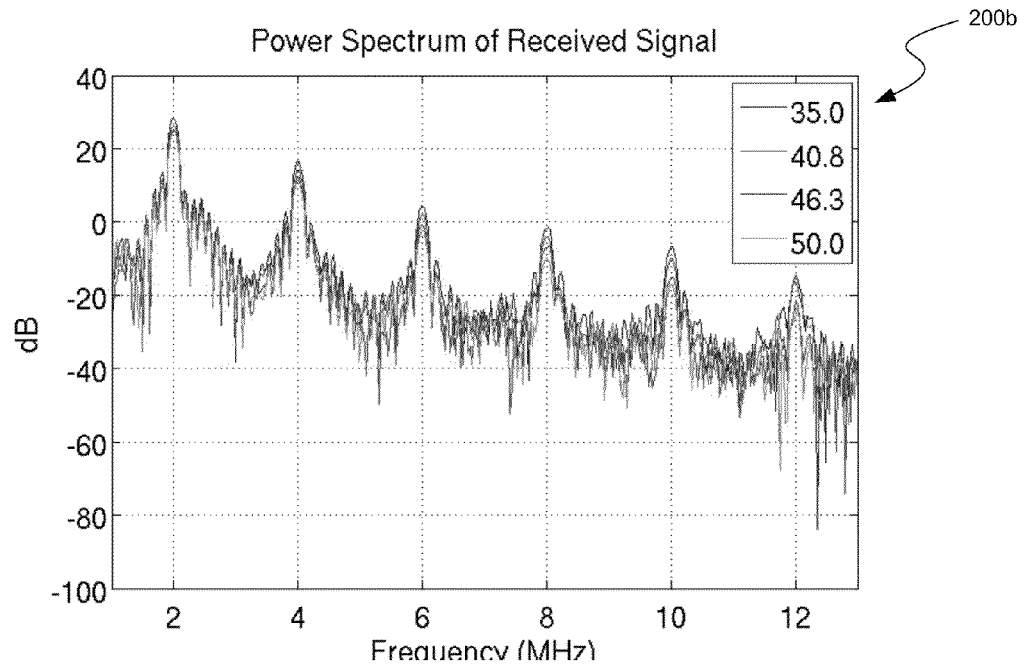
FIG. 2B is a graph illustrating a power spectrum of the detected ultrasound signals of FIG. 2A in accordance with an embodiment of the present technology.
Figure 3A:
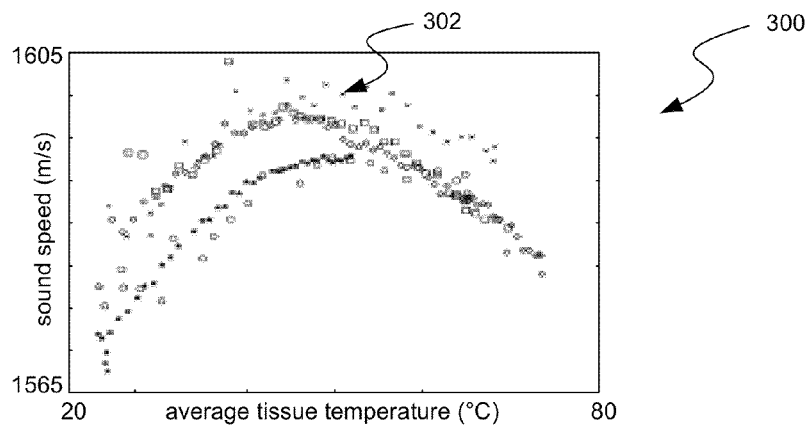
FIG. 3A is graph illustrating sound speed as a function of tissue temperature in accordance with an embodiment of the present technology.

This correlation between the attenuation in tissue and temperature, as well as the relationship between sound speed and temperature, are demonstrated in FIGS. 2A and 2B. More specifically, FIG. 2A is a graph 200*a* illustrating a time series of ultrasound signals as a function of increased tissue temperature (i.e., from 35.0° C. to 50.0° C.), and FIG. 2B is a graph 200*b* illustrating the associated power spectrum of the ultrasound signals in accordance with an embodiment of the present technology. The graphs 200*a-b* can include color-coded channels, each associated with a different tissue temperature value (i.e., 35.0° C., 40.8° C., 46.3° C. and 50.0° C.) measured during the application of HIFU pulses (e.g., 2 MHz, 15 cycles pulse). As shown in FIG. 2A, the pulses shift to the left of the graph 200*a* as tissue temperature increases from 35.0° C. (a blue curve 203) to 46.3° C. (a red curve 201). This indicates that sound travels faster in tissue as the tissue temperature increases. However, as further shown in FIG. 2A, the time shift of the ultrasound signal nears zero between 46.3° C. and 50.0° C. (i.e., the red channel 201 and an aquamarine channel 205 have approximately the same position with respect to their position on the x-axis of the graph 200*a*). This corresponds to a plateau region 302 in the temperature vs. sound graph 300 shown in FIG. 3A. As shown in FIG. 3A, the plateau region 302 and the following decrease in the sound speed illustrates the temperature at which it becomes difficult to correlate sound speed to tissue temperature.

Referring back to FIG. 2A, the graph 200*a* also illustrates that the amplitude of the signal decreases as the temperature of the tissue increases. For example, the signal of the red channel 201 (measured at a tissue temperature of 46.3° C.) has a smaller amplitude than the signal of the blue channel 203 (measured at a tissue temperature of 35.0° C.), and this correlates to a decreasing power of the harmonics as shown in FIG. 2B. Accordingly, the attenuation of higher harmonics increases as temperature increases. Unlike sound speed, these differences in the magnitudes of the higher harmonics in their power spectra remain significant and quantifiable at higher temperatures (e.g., as indicated by the difference in amplitude of the red channel 201 and the aquamarine channel 205). The method 100 (FIG. 1) uses this characteristic to remotely infer the in-situ tissue temperature by tracking the relative changes in the magnitudes of the higher harmonics from consecutive frames, a reference frame, or both.

Figure 3B:
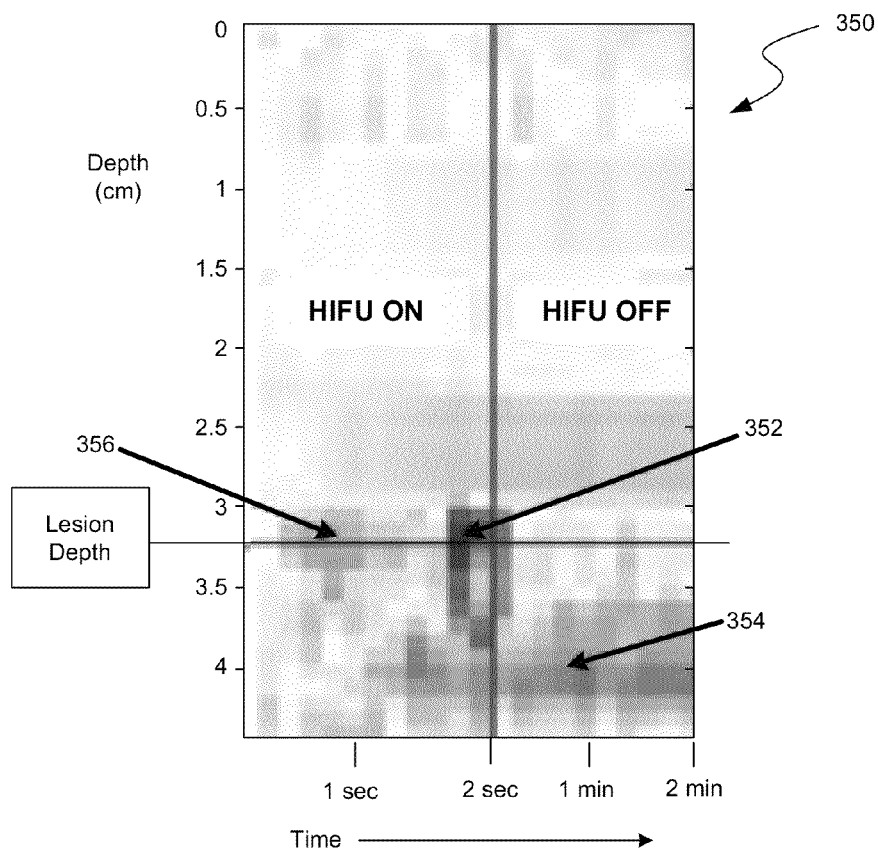
FIG. 3B is an M-mode color display configured in accordance with an embodiment of the present technology.

The graphs 200a-b shown in FIGS. 2A and 2B can be formed from a spectral color M-mode display, which can also be used to visually track temperature during HIFU therapy. The M-mode display is made using backscattered ultrasound signals recorded by an ultrasound imaging probe. The received signals can be divided into three spectral bands, and the power in each assigned to a red, green, or blue additive color channel. By normalizing a spectrum from a region of interest by its reference frame counterpart (e.g., the scan line collected before HIFU therapy), the spectral temporal evolution can be visualized, with color representing power excess in a band. For example, such an M-mode color display 350 is illustrated in FIG. 3B, which can be used for-real time image guidance and automated control of heat-induced therapy (e.g., HIFU therapy). The M-mode color display 350 shows a focal region 352 of increased backscattering and harmonics due to bubbles, decreased high frequency content at a region 354 beyond the focal region 352, and another area 356 of increased high frequency content proximate the focal region 352. These spectral-color pixels can then be mapped in 2-D in time and space to create the graphs 200a-b shown in FIGS. 2A and 2B. This spectral technique is less sensitive to misregistration and motion artifacts than RF correlation processing because the spectral magnitudes are obtained by integration over a depth interval of, e.g., several millimeters.

Referring back to FIG. 1, once the tissue temperature has been determined, the method 100 can further include forming a temperature profile of a region of interest using the received signal (block 108). For example, the magnitude and/or phase of a set of three harmonic components (i.e., the 1st-3rd harmonics, 2nd-4th, 3rd-5th harmonics, etc.) can be encoded into an RGB additive color channel, beamformed using a pixel-based beamformer, and displayed on a screen or monitor as a two-dimensional (2-D) color image (e.g., the M-mode color display 350 shown in FIG. 3B). Since increases in temperature increase acoustic attenuation and higher harmonics are most sensitive to this change in attenuation, any temperature changes in the tissue at the region of interest will become visible in the 2-D color image, and will change dynamically from frame to frame as the tissue temperature changes. As described in further detail below, in other embodiments the spectral-based temperature estimation can be used to form 3-D temperature displays of the region of interest to monitor temperature during treatment. These 2-D and/or 3-D images can be used during HIFU and/or other temperature-induced therapies to dynamically track and visualize the temperature profile of a region of interest.

Accordingly, the method 100 can be used to track spectral changes in harmonic content to provide direct temperature estimations and, optionally, display the changes in tissue temperature as a dynamic 2-D and/or 3-D image. As discussed above, the spectral-based method 100 can track the high tissue temperatures reached during HIFU and other targeted energy therapies, such as temperatures above the coagulation threshold of a tissue (e.g., greater than 50° C.). The method 100 is also generally unaffected by target movement (e.g., a tumor, tissue mass, etc.) since the spectral content of the nonlinear ultrasound waves are obtained by integration over a depth.

Moreover, since the temperature estimation method 100 uses ultrasound imaging systems to detect the spectral changes, the method 100 provides a more cost-effective and convenient approach to temperature monitoring than MRI-based techniques. For example, ultrasound systems are relatively inexpensive and generally more portable than MRI systems. When ultrasound energy is used as the modality for temperature-induced tissue therapy, the ultrasound imaging hardware can be integrated into the same assembly as the therapeutic ultrasound hardware, thereby reducing the overall size and maneuverability of the devices. Whether used independently or combined with the therapeutic ultrasound system, the ultrasound-based imaging and therapeutic systems allow for a plug-and-play type system in which the ultrasound imaging system is compatible with the therapeutic ultrasound system and only requires additional software to process the received data (e.g., to provide temperature estimations). In addition, therapeutic ultrasound and/or other heat therapy systems that use the method 100 to monitor temperature must not be magnet-compatible (as is required for MRI monitoring). Moreover, the effects of misregistration and path distortion are reduced or minimized when the therapeutic and monitoring systems are based on the same modality (i.e., ultrasound) because both the therapy and imaging beams undergo similar distortions and therefore remain registered with respect to one another.

In various embodiments, the method 100 can be used to form a calibration look-up or reference table that quantifies changes in harmonic magnitudes with temperature variations. Such a reference table can be derived through experiments using a tissue phantom and/or numerical simulations (described below), and can subsequently be used to provide quantitative temperature information. For example, the reference table can be used during HIFU and/or other targeted energy therapies to track the changes in tissue temperature associated with the measured harmonic magnitude. Similar reference tables can also be provided for various slopes between selected harmonics and/or other nonlinear acoustic quantities associated with changes in temperature.

Simulations of RF Imaging Data

Computer simulations can be performed to predict the temperature at a treatment site during a heat-induced therapy using selected treatment parameters and tissue properties. For example, time-domain software (e.g., Acoustic Virtual Laboratory made by LMS International of Leuven, Belgium) can be used to model high intensity therapeutic applications of ultrasound and its interaction with biological media. In a particular embodiment, the software is based on 2-D, 2.5-D (cylindrical symmetry), or 3-D full-wave acoustic propagation in inhomogeneous, lossy media coupled with tissue-specific heat transfer laws for isotropic, inhomogeneous materials. The model can include nonlinear acoustic propagation, frequency dependent power-law losses typical of biological media, diffraction, and reflection/scattering effects. The acoustic component of the software can be coupled with a fully inhomogeneous bio-heat transfer model to determine temperature development and evolution due to the applied acoustic fields. The heat transfer component can be configured to include perfusion effects in soft tissue where it is assumed that the blood within capillary beds equilibrates instantaneously with the temperature of the surrounding medium. The heat transfer component can also model fluid advection processes (e.g., flow within an artery) in finite dimension blood vessels where there is no instantaneous temperature equilibrium. The software may also provide for simulations of various ultrasound transducers (e.g., different beam shapes, frequencies, etc.) and of various heterogeneous geometries. In addition, the software can provide output data for spatial distribution at fixed times of various variables (e.g., pressure, intensity, temperature, etc.) and time signals at fixed spatial locations. In various embodiments, the computer-simulated model may be configured to reflect different degrees of complexity in the dependence of sound speed on temperature (e.g., as explained in further detail below), allow attenuation to change with temperature, allow for the appearance of bubbles, and/or allow for other suitable characteristics of heat-induced therapies.

Simulation software can also be used for imaging purposes. For example, RF backscatter data may be simulated using a random assortment of point scatterers fixed to a numerical grid and a conventional convolutional model using the transmit/receive bandwidth of a particular ultrasound imaging device. Using the simulated RF data can provide highly controlled numerical testing for temperature estimation algorithms and increased freedom in testing and optimizing different solutions for coded excitation (described below).

Selected Embodiments of Ultrasound Transducer Devices for Temperature Estimation One or more ultrasound transducer devices can be used to (1) provide adequate energy transmission to propagate nonlinear waves, and (2) adequately capture the frequency rich content of a received echo after it undergoes nonlinear propagation. Conventional ultrasound probes are designed to operate on a limited bandwidth centered at the operating frequency, and therefore typically lack the sensitivity to detect meaningful amounts of harmonic scatter. However, a multi-layered ultrasound transducer device can be configured to (1) transmit a narrow bandwidth signal that provides a high conversion efficiency and high power ultrasound waves, and (2) receive a wide bandwidth to capture the harmonic content in the echoes of the ultrasound waves to enable the temperature estimation described herein (e.g., the temperature estimation method 100 described with reference to FIG. 1).

Figure 4A:
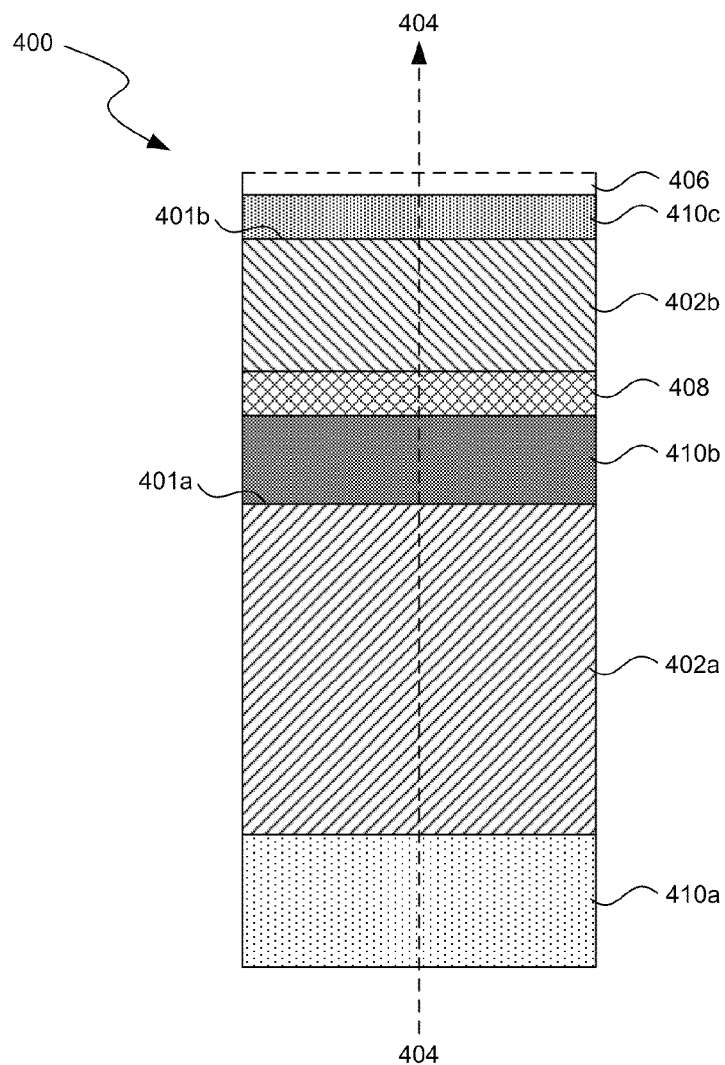
FIGS. 4A and 4B are schematic views of an ultrasound transducer device for real-time temperature estimation in accordance with an embodiment of the present technology.
Figure 4B:
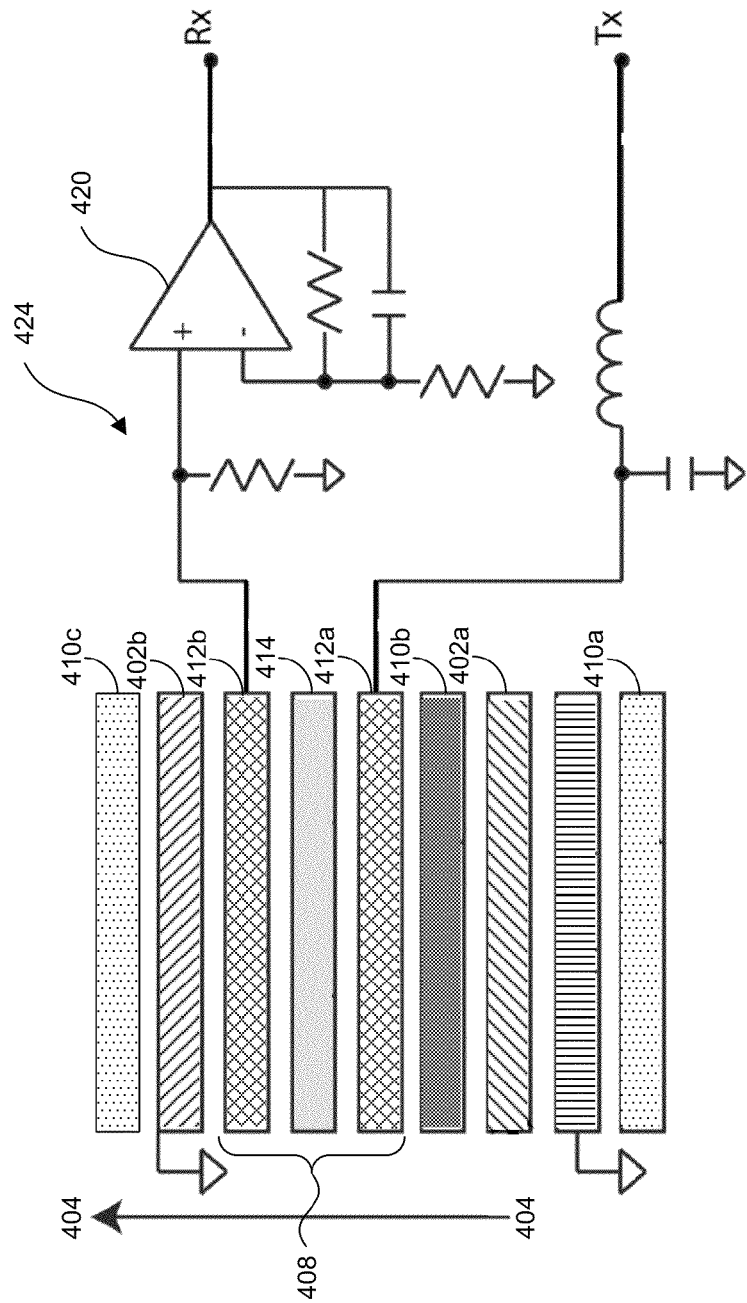

FIGS. 4A and 4B, for example, are schematic views of such a multi-layer ultrasound transducer device 400 ("transducer device 400") configured in accordance with an embodiment of the present technology. Referring to FIG. 4A, the transducer device 400 can include a first transducer 402a that transmits high power ultrasound waves and a second transducer 402b that has a wide bandwidth for receiving the harmonics of the reflected ultrasound waves. The first transducer 402a and the second transducer 402b can have corresponding first and second surfaces 401a and 401b that are oriented substantially parallel to one another and normal to an acoustic axis 404-404. This allows the high energy ultrasound waves to exit the transducer device 400 through an aperture 406 positioned over the first and second transducers 402a-b (as indicated by the arrow on the acoustic axis 404-404), and the reflected signals to enter the transducer device 400 via the same aperture 406 (in the opposite direction of the arrow). The second transducer 402b can be relatively thin (e.g., acoustically transparent) such that its placement in front of the first transducer 402a does not have a significant effect on the transmit characteristics of the transducer device 400. As further shown in FIG. 4A, the transducer device 400 can also include an electrical connection layer 408 positioned between the first and second transducers 402a-b and impedance matching layers 410 (identified individually as first through third impedance matching layers 410a-c, respectively) positioned around and between the transducers 402a-b. For illustrative purposes, the transducer device 400 shown in FIGS. 4A and 4B includes one multi-layered transducer element (i.e., the co-aligned first and second transducers 402a-b), but other transducer devices configured in accordance with the present technology can include a plurality of multi-layer transducer elements, such as a 32-element array, a 128-element array, and/or arrays having more or less multi-layer transducer elements. Multi-element arrays can provide an increased imaging depth (e.g., for treatment of deeper organs, such as the liver, spleen, kidney, etc.), better lateral and axial resolution, and more power to generate nonlinear effects.

The first transducer 402a can be composed of a first piezoelectric material that can be configured to transmit ultrasound waves that become nonlinear through propagation and, optionally, receive echoes of the ultrasound wave it transmits. The first piezoelectric material, for example, can be a piezoceramic, such as lead-zirconate-titanate (PZT) or a compound thereof, that has a high electro-acoustic conversion efficiency and may also receive reflected ultrasound waves. In other embodiments, however, the first piezoelectric material can be used solely to transmit ultrasound waves. In further embodiments, the first transducer 402a can be made from other ceramic or non-ceramic piezoelectric compounds, single crystals (e.g., isotropic amorphous ceramics), and/or other suitable piezoelectric materials with high electro-acoustic conversion efficiencies for transmitting acoustic waves.

The second transducer 402b can be composed of a second piezoelectric material that has a wide bandwidth for receiving echoes with rich frequency content from the reflected ultrasound waves. In selected embodiments, for example, the second piezoelectric material can have a bandwidth of approximately 20 MHz, approximately 40 MHz, or higher. The wide bandwidth allows the second transducer 402b to receive the third harmonic of the transmit frequency or higher dependent upon the acoustic properties of the transmit medium. In other embodiments, the bandwidth of the second piezoelectric material can be lower than 20 MHz, but still suitable for receiving multiple harmonics.

The second transducer 402b can be made from piezopolymer materials, such as polyvinylidene fluoride (PVDF) and/or a co-polymer of PVDF with Trifloroethylene (PVDF-TrFE). These materials exhibit a strong piezoelectric response and have an acoustic impedance that is closer to water than other piezoelectric materials (e.g., PZT), making them suitable sensors for ultrasound waves propagating in a medium with acoustic impedance similar to water (e.g., human soft tissue). In other embodiments, the second transducer 402b can include other copolymers and/or other suitable materials that have a wide bandwidth.

In the embodiment illustrated in FIG. 4A, the second transducer 402b is positioned over and substantially co-aligned with the first transducer 402a. The acoustic waves transmitted by the first transducer 402a must, therefore, propagate through the second transducer 402b before exiting the transducer device 400 via the aperture 406. Accordingly, the second transducer 402b can be made from a thin layer of the second piezoelectric material such that it has a substantially negligible effect (e.g., minimal attenuation) on the transmitted wave. In selected embodiments, for example, the second transducer 402b can have a thickness of approximately 110 μm or less. In other embodiments, the second transducer 402b may be thicker than 110 μm, but still have a substantially negligible effect on the transmitted wave. In other embodiments, the first and second transducers 402a-b can be laterally offset, side-by-side, staggered, and/or otherwise oriented with respect to one another.

As shown in FIGS. 4A and 4B, the electrical connection layer 408 can be positioned between the first and second transducers 402a-b and electrically coupled to each such that it can route electrical connections to the transducers 402a-b. Referring to FIG. 4B, the electrical connection layers 408 can be patterned with first channels 412a and second channels 412b (e.g., traces) that are electrically isolated from one another by an insulating layer 414. The electrical connection layer 408, for example, can be a thin flex circuit (e.g., a flex circuit manufactured by Microconnex, Inc. of Snoqualmie, Wash.) that includes traces (e.g., copper, gold, etc.) isolated from one another by a polymer material and/or other flexible and insulative material. The first and second channels 412a and 412b can be separately connected to the corresponding transducers 402a-b such that the first channels 412a route transmit signals (Tx) to and from the first transducer 402a and the second channels 412b route receive signals (Rx) to and from the second transducer 402b. In various embodiments, such as when the first and second transducers 402a-b are substantially co-aligned, the first channels 412a can also route receive signals (Rx) to and from the first transducer 402a.

As shown in FIG. 4B, second channels 412b of the electrical connection layer 408 can be coupled to an impedance matching circuit 424 (e.g., on a printed circuit board ("PCB")) to isolate the second transducer 402b from the receive circuitry at a programmable imager (e.g., a computer display). The second transducer 402b can also be coupled via the second channels 412b to a high impedance input of a non-inverting operational amplifier 420. The proximity of the second channels 412b to the second transducer 402b and the amplifier 420 (e.g., in a housing or handle of the transducer device 400) allows the amplifier 420 to improve the receive sensitivity of the second transducer 402a.

In some embodiments, the first transducer 402a, because of its band-limited characteristics and its good efficiency in electrical-mechanical-electrical transduction and power transfer, is used in a transmit/receive mode to generate the interrogating signal and create the B-mode image at the fundamental frequency. In such embodiments, the second transducer 402b, because of its broadband characteristics, good mechanical-electrical transduction, and relatively low power transfer in transmit mode, is only used in a receive mode to capture the higher frequency content of the echo. The received harmonics can then be processed differentially for standard B-mode harmonic imaging and for temperature estimation. In various embodiments, a programmable ultrasound engine (e.g., a Verasonics Ultrasound Engine made by Verasonics, Inc. of Redmond, Wash.) can use flash imaging with very high frame rates (e.g., up to 6 KHz), interleaving of frame acquisition between the transmit and receive subsystems at rates of, e.g., greater than 120 Hz to provide real-time monitoring. Further features of the transducer device 400 and related multi-layer ultrasound transducer devices are described in U.S. patent application Ser. No. 13/158,299, filed Jun. 10, 2011, and entitled "MULTILAYER ULTRASOUND TRANSDUCER DEVICES FOR HIGH POWER TRANSMISSION AND WIDE-BANDWIDTH RECEPTION AND ASSOCIATED SYSTEMS AND METHODS," incorporated herein by reference in its entirety. In other embodiments, the temperature estimation methods disclosed herein can be performed by other ultrasound transducers configured to transmit high energy ultrasound waves and/or detect a broad bandwidth of the echoes.

Figure 5:
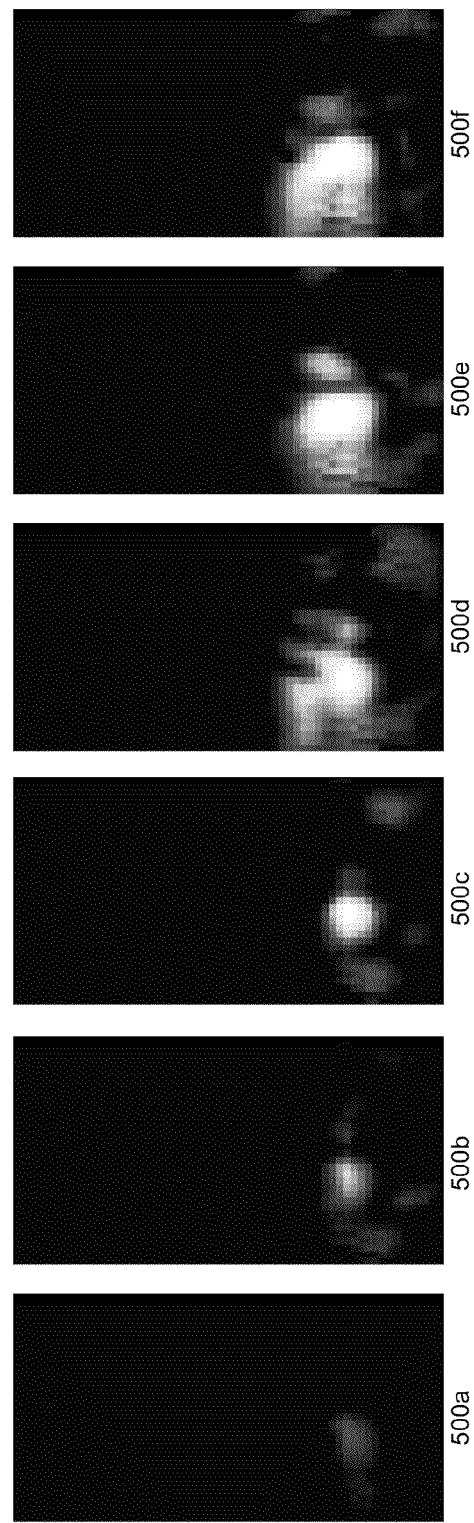
FIG. 5 is a series of images representing the change in tissue temperature during HIFU therapy taken using a multi-layered ultrasound device configured in accordance with an embodiment of the present technology.

FIG. 5 is a series of images 500a-f of a treatment site during HIFU therapy taken by a multi-layer ultrasound transducer device (e.g., the transducer device 400 described above) in accordance with an embodiment of the present technology. The images 500a-f illustrate the time evolution of the local temperature rise in tissue for a HIFU therapy of approximated 30 seconds at medium power. As shown in FIG. 5, the multilayer ultrasound device can track the focal area of the HIFU source and the diffusion of heat as time increases. It is also sufficiently sensitive enough to track temperature changes at lower temperatures (e.g., before a thermal legion has formed) and at higher temperatures.

In other embodiments, temperature estimation and tracking can be performed by other suitable ultrasound devices that can record higher harmonics. The ultrasound device can propagate its own high energy signal from which the higher harmonics are recorded and/or record the harmonics of the ultrasound signal produced by the therapeutic ultrasound device.

Selected Embodiments of Transmit Pulse Sequences and Echo Analysis

The transmit pulse sequence of an ultrasound transducer device (e.g., the transducer device 400 of FIGS. 4A and 4B) can be selected to enhance the signal-to-noise ratio and/or emphasize the higher harmonic content of the echo signal. In various embodiments, for example, a pulse inversion method can be used to isolate harmonic content in the received signal. The pulse inversion method can include transmitting consecutive identical pulses of ultrasound energy, each pulse having an inverse polarity of the previous pulse, such that the harmonics are generated out of phase during nonlinear propagation. Summing the received echoes from two consecutive pulses cancels the fundamental, and therefore the received signal isolates the nonlinear effects. Conventional pulse inversion methods, however, only emphasize even harmonics and cancel out odd harmonics (e.g., including the fundamental). This effectively reduces the frequency content of the received signal by half, and thereby reduces the sensitivity to changes in the harmonic content used during the spectral-based temperature estimation method described above.

A pulse inversion sequence can be modified to include amplitude modulation to obviate the loss of harmonic content. Similar to conventional pulse inversion methods, this modified pulse inversion method can propagate consecutive identical but inverse pulses. However, the reference pulse can be transmitted at a low amplitude and the inverted pulse can be transmitted at a high amplitude, or vice versa. The lower amplitude signal propagates at least substantially linearly and remains centered at the fundamental frequency. During the detection of the echo, the lower amplitude signal can be amplified to the level of the higher amplitude signal and subtracted from it, thereby effectively suppressing only the fundamental component and providing a full spectrum harmonic content (e.g., both even and odd harmonics).

Due to the summing of consecutive inverted pulses, the frame rate of both the modified and conventional pulse inversion methods is reduced by a factor of two. However, a high frame rate may not be necessary for real-time temperature estimation purposes due to the relatively large heat diffusion constant. In addition, reducing the size or volume of the region of interest for imaging purposes allows for an increase in frame rate. For example, the imaging region of interest during HIFU therapy can be restricted to or near the small focal region of a HIFU applicator. When a higher frame rate is desired, a programmable ultrasound engine with a high frame rate (e.g., an ultrasound engine made by Verasonics of Redmond, Wash.) can be used to generate a pulse inversion sequence, and compensate for the reduced frame rate to provide real-time echo feedback.

In other embodiments, a coded excitation method can be used to generate a suitable pulse sequence. Coded excitation methods include the design of an interrogating chirp signal and the design of a corresponding compression filter that removes the frequency coding in the signal echoes and recovers the desired axial resolution. Typically, the chirp signal is implemented as a long, linear frequency-modulated burst into a medium (e.g., tissue). The main design parameters of the chirp are length and bandwidth, which can be used to determine the energy contained in the chirp and the maximum obtainable axial resolution after compression, respectively. The design of the compression filter is typically based on a matched-filter approach, which uses an autocorrelation filter having an impulse response that is the time inverse of the transmitted chirp. Typically, the compression filter has the same bandwidth as the fundamental of the transmitted chirp. This serves to extract the fundamental frequency from the echo signal, adjust the phase of the frequency components, and thereby isolate the nonlinear components of the received echo.

In various embodiments, a nonlinear compression filter can be used to selectively extract and compress the higher harmonics from the received echo, and therefore the resultant coded excitation method is not restricted to the initial bandwidth of the transmit chirp and does not lose the harmonic content generated by nonlinear propagation. For example, the transmit chirp described above can still be used as the transmitted coded signal, but decoding of the echo can be achieved by parallel matched-filter banks that have two, three, four or more times the instantaneous frequency at every time point. The echo can be properly apodized to reduce range side lobes and maintain the same frequency bandwidth as if the coded signal frequency were doubled, tripled, quadrupled, etc. For example, when a transmit chirp has a frequency range of about 2-4 MHz, the compression filters can have a frequency range of about 4-8 MHz, 6-12 MHz, and 8-16 MHz, respectively. From a frequency domain perspective, this implementation is equivalent to compression filters that selectively extract and compress the second, third, and fourth harmonic from the echo signal. These compressed signals maintain good axial resolution and center frequencies at the second, third, and fourth harmonic of the transmitted chirp. This increase in frequency provides an increased signal-to-noise ratio that enhances the detection of the relative changes in the higher harmonics frequency bands. Accordingly, the frequency-enhanced coded excitation sequences can facilitate frequency deconvolution for spectral temperature estimations (e.g., the method 100 described above).

Selected Embodiments of Temperature Estimation Using Spectral Indicators

Once a suitable pulse sequence has been applied, the nonlinear information can be extracted from the received echo, which may be subject to the effects of frequency-dependant attenuation, depth-dependant attenuation, and signal-to-noise degradation. For example, in some embodiments wavelet analysis can be used to analyze echo signals. Wavelet transforms can map low wavenumber information of received signals into coarsely sampled subspaces spanned by larger scale wavelet bases, and can map high wavenumber information into more finely sampled subspaces spanned by shorter wavelet bases. Such wavelet analysis can treat a compression filter as a blind deconvolution filter to maintain a suitable resolution, and also increase the signal-to-noise ratio using the coded excitation methods described above. In various embodiments, the wavelet analysis can also use a linear filter, which is by nature time-invariant (i.e., filter coefficients are not a function of time), to filter the echo signal as a whole. In other embodiments, depth-dependent filters can be used during wavelet analysis to provide a time-frequency analysis, and/or other suitable filters can be used for wavelet analysis.

During wavelet analysis, a signal is typically decomposed at different scales using a mother wavelet that is at least generally similar to the original waveform. However, the received signal (i.e., ultrasonic RF data) used for temperature estimation is not symmetrical, and therefore it would be inefficient to select a standard mother wavelet with symmetry (e.g., a Mexican hat waveform, Morlet waveform, etc.). Instead, wavelet analysis can use a fast lifted interpolating wavelet transform ("LIWT") that is based on a lifting scheme applied to second-generation wavelets. The second-generation wavelets do not include dilates or translates of a single mother wavelet, but instead are constructed exclusively in the signal domain using lifting. Therefore, the second-generation wavelets basis function can be custom designed for complex signals (e.g., those provided in a nonlinear echo signal). This wavelet analysis allows for frequency filtering as a function of time using a tailored model because the lifting scheme is based directly on the features of the signal itself Wavelet analysis allows frequency resolution and time resolution to remain proportionate to scale. This is in contrast to the standard time-frequency spectrogram in which resolution in frequency and time are inversely dependent (e.g., increased resolution in frequency results in a decreased resolution in time). The proportionate frequency and time resolution results in an overall quasi-constant fractional resolution suitable for ultrasound imaging, in which a fractional bandwidth is often a good indication of the axial resolution of an ultrasound image produced by an ultrasound transducer. This enhanced resolution provides greater freedom for processing echo signals.

In various embodiments, wavelet signal processing can also be used to denoise received echo signals before compression filtering and analysis. For example, wavelet signal processing can include selecting a wavelet coefficient to compensate for degradation in the signal-to-noise ratio (e.g., due to depth and frequency attenuation), and therefore any signal processing on the wavelet-decomposed signal can be done by a simple manipulation of the wavelet coefficients. In some embodiments, for example, denoising can be performed using a hard threshold approach in which wavelet coefficients are set to zero if their magnitude is below the threshold.

Selected Embodiments of Temperature Estimation Using Apparent Strain

The spectral-based temperature estimation approach described above may be supplemented by or used in conjunction with a strain-based approach. Strain-based cross-correlation methods use time series information obtained from raw RF data (e.g., acoustic travel time) to extract temperature information. In some embodiments, apparent strain can be estimated by tracking changes in acoustic travel time between corresponding ultrasound scan lines on temporally adjacent RF data frames. For example, RF voltage time series can be reconstructed for each scan line in each RF frame and subdivided into a series of segments of length (e.g., 1 mm with 20% overlap). For each segment, a 1-D cross-correlation can be used to find the best match within a search region defined around the same spatial location on a temporally adjacent frame acquired later in time. Time shifts can be estimated using a polynomial spline matched to several points in the cross-correlation. The time shift for which the best match was obtained is the estimated travel time change for the segment.

This procedure can be repeated for all segments in a frame to obtain a 2-D travel time change map corresponding to two temporally adjacent RF frames. Results from consecutive pairs of frames can be integrated in time to provide 2-D maps of the accumulated travel time changes for any given frame. To reduce the effects of noise, a local strain estimation can be performed by differentiation in depth (e.g., using a least squares algorithm). For example, FIG. 6 illustrates a series of images 600a-d that show the change in local acoustic travel time due to temperature rise estimated using such a cross-correlation method.

Figure 6:
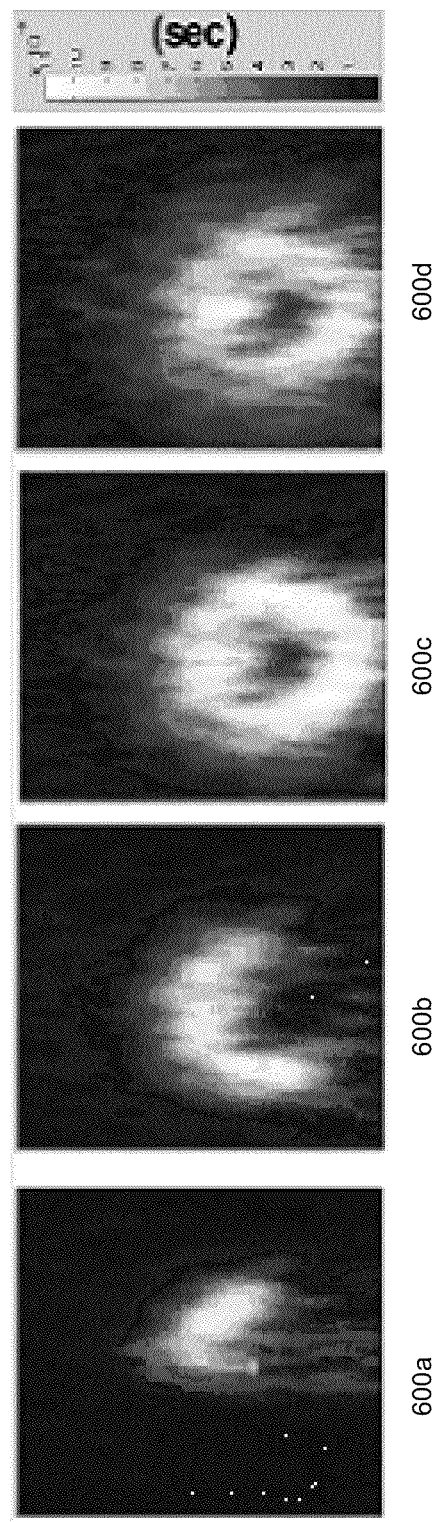
FIG. 6 is a series of images representing changes in tissue temperature during HIFU therapy estimated based on local acoustic travel time in accordance with an embodiment of the present technology.

While FIG. 6 illustrates that strain-based approaches can be used to estimate temperature, strain-based cross-correlation methods over extended periods of time are sensitive to both endogenous and exogenous motion, and therefore may hinder the accuracy of the temperature estimates. For example, temperature estimations at a greater depth may be subject to more movement, and therefore strain-based cross-correlation methods may not provide accurate temperature estimates. To mitigate the effects of motion, bio-heat transfer equations temperature simulations can be used to invert for temperature by using the travel-time data directly. Alternatively or additionally, apparent strain data can be used to invert for temperature, thereby providing reduced computations for temperature estimation and reducing the decorrelation effects of motion.

As discussed above and as shown in FIG. 3, acoustic travel time has a relatively low sensitivity at higher temperatures (e.g., the temperatures used during HIFU therapies), and the relationship between sound speed and temperature diminishes above the coagulation threshold temperature. The multi-valued relationship between temperature and acoustic speed can be mitigated by using a non-local approach to the inversion, meaning that the temperature field must be continuous and subject to the smoothing effect of heat diffusion. This constraint can be applied to tissue temperature in 3-D, and may permit continuation of the temperature field into the plateau region 305 (i.e., near 50°) and higher (e.g., to the temperature at the HIFU focus).

Combining Strain Information and Spectral Signatures for Quantitative Temperature Mapping.

As discussed above, strain-based information can be sensitive to movement and has a multi-valued relationship with temperature. Spectral-based information may include aliasing effects due to increases in proximal attenuation and hysteretic effects in the attenuation when tissue undergoes denaturation. For example, increases in proximal attenuation can affect distal locations independently of the local temperature. That is, attenuation changes at a given location modify the spectral content of the signal from a location further along the propagation path. Accordingly, strain and spectral information can be compounded and correlated with both strain-based and spectral-based temperature calibration maps (e.g., experimentally obtained and/or simulated) and with previous compounded reference frames (i.e., in earlier periods of time) to quantify temperature changes.

In some embodiments, weighting parameters may be used to emphasize either one process or the other as necessary. For example, strain-based temperature estimations can have a higher weighting factor than spectral-based estimations in regions proximate to the source of the transmitted wave because this region is subject to less movement and the nonlinear effects necessary for spectral-based estimations may not yet have developed. Spectral-based temperature estimations can have a higher weighting factor at a region positioned at a depth in the tissue, i.e., where nonlinear effects have taken place and more movement occurs. This combination of strain- and spectral-based temperature estimation methods can improve temperature estimation accuracy and/or real-time treatment monitoring.

Resolution and Motion Artifacts

Spatial and lateral resolutions depend, at least in part, on the methods used for the excitation pulse and echo analysis described above. In some embodiments, the transmit pulse can be relatively long (e.g., 5-10 cycles; similar to those used for Color Doppler visualization), have a frequency of approximately 2 MHz, and the ultrasound transducer device can operate at an F-number between about 1.0 and about 1.5. Such transmit pulses may provide an axial resolution of less than approximately 1 mm and a lateral resolution of about 0.5 mm at the fundamental frequency. The nonlinear content of the signal may provide an actual spatial resolution that is significantly higher. In other embodiments, the spatial resolution can be lower or higher.

Temperature resolution can also depend on the selected transmit pulse and the echo analysis. In some embodiments, for example, the temperature estimation methods described above can detect temperature changes of about 5° C. for temperatures ranging from about 35° C. to about 50° C. In other embodiments, the temperature estimation methods can resolve temperature changes of a minimum of about 1-2° C. in the full clinical temperature range of 35-90° C. In further embodiments, temperature estimation methods can have higher or lower resolutions and/or estimate temperature at higher or lower ranges.

In various embodiments, strain-spectral compounding can be used to isolate the confounding effects of motion and deformation using methods, and thereby enhance temperature and/or spatial resolution(s). As described above, motion artifacts can have a significant effect on strain-based temperature estimations, but do not significantly influence spectral content and the relative magnitude of the harmonics in the returned signal. This allows for the decorrelation of a strain-based estimate that is not supported by estimated changes in the spectral domain. Accordingly, strain-spectral based temperature estimation can detect, isolate, and eliminate extrinsic motion artifacts from the temperature estimation.

3-D Ultrasound Imaging and 3-D Temperature Mapping

The temperature estimation methods described above can be used to image and estimate temperatures in three dimensional space to aid treatment monitoring and guidance. In some embodiments, 3-D ultrasound imaging can be performed with freehand 3-D ultrasound imaging systems. When a 1D linear PZT-PVDF probe is used to obtain spectral and/or strain information (e.g., the multi-layered transducer device 400 shown in FIGS. 4A and 4B), a 3-D ultrasound display can be formed based on 2-D imaging techniques with additional spatial tracking. For example, a 3-D ultrasound imaging system (e.g., an HDI 5000 ultrasound imager made by Phillips Healthcare of The Netherlands) can be communicatively coupled to a magnetic tracking system to register 2-D images in a 3-D coordinate system. The images can be captured on a computer by a frame-grabber from the video output of the ultrasound imaging scanner, and the system can track and record the 3-D position (x, y, z coordinates) and orientation (roll, pitch, yaw of the receiver axes relative to the transmitter axes) of each 2-D image. Various software programs can manipulate the captured data to form a 3-D image of the region of interest (e.g., using Visual C# made by Microsoft, Corp. of Redmond, Wash.). The 3-D image can be superimposed with and display dynamic quantitative temperature data using surface and/or volume reconstruction.

In other embodiments, an imaging assembly (e.g., the transducer device 400 of FIGS. 4A and 4B) can be combined with a HIFU and/or other suitable energy source, and the assembly can be mounted or otherwise attached to an articulated arm that can be used to track the position of the assembly. The articulated arm can provide flexible positioning, provide high accuracy, and avoid the line of sight and metallic interference limitations associated with optical and magnetic trackers, respectively. In one embodiment, for example, an imaging and HIFU transducer can be attached to a MicroScribe© G2X 3-D digitizing arm made by CNC Services, Inc. of Amherst, Va., and may be integrated with 3-D image capture software, which can provide a 6D spatial measurement output (i.e., coordinates (x, y, z) and orientations (roll, pitch, yaw)). In some embodiments, the 3-D ultrasound system provided by an articulated arm and combined with magnetic tracking can provide 0.1 mm accuracy±1 mm precision.

During a HIFU or other energy-based therapy, the articulated arm or other suitable device can provide a continuous sweep of the imaging transducer across a region of interest to provide the images to generate a 3-D volume reconstruction of the region of interest. This 3-D volume can be displayed on, e.g., a screen or monitor, and the location of the current image plane displayed on the monitor in real time within the volume. In various embodiments, the graphical displays can include transparent volume rendering, surface renderings of the region of interest, orthogonal planar slicing, a combination of these and/or other suitable types of displays for image guidance and monitoring treatment progress. In some embodiments, an isosurface display can be used for temperature visualization. For example, the displayed volume can include a surface that is color-coded according to the value of the temperature measured. Orthogonal slicing can also be incorporated to allow the operator to navigate within the volume and monitor treatment at specific sites of interest. Suitable volume visualization algorithms can be developed using Visualization Toolkit software made by Kitware, Inc. of Clifton Park, N.Y. In other embodiments, real-time 3-D imaging can be provided using data collected from 2-D imaging probes, and the reconstruction and rendering can be applied directly to the data.

Conclusion

From the foregoing, it will be appreciated that specific embodiments of the technology have been described herein for purposes of illustration, but that various modifications may be made without deviating from the disclosure. Certain aspects of the new technology described in the context of particular embodiments may be combined or eliminated in other embodiments. Additionally, while advantages associated with certain embodiments of the new technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. A method for real-time noninvasive temperature estimation, the method comprising:
    propagating ultrasound waves into tissue, wherein the ultrasound waves become nonlinear in the tissue;
    detecting echoes of the ultrasound waves, wherein detecting the echoes comprises detecting a plurality of harmonics of the ultrasound waves; and
    monitoring changes in tissue temperature in real-time during treatment using a spectral-based approach, wherein monitoring the changes comprises monitoring changes in the magnitude of at least one detected harmonic to estimate tissue temperature, and wherein greater attenuation of an individual harmonic correlates to an increase in the tissue temperature.

2. The method of claim 1, further comprising:
    providing a plurality of predefined changes in harmonic magnitudes that correspond with predefined changes in tissue temperature; and
    correlating a change in the magnitude of a detected harmonic with a predefined change in tissue temperature to determine the tissue temperature.

3. The method of claim 1 wherein monitoring the changes in tissue temperature comprises monitoring tissue temperatures above 60° C. in real-time.

4. The method of claim 1 wherein:
    the ultrasound waves become non-linear proximate to a focal region in the tissue;
    monitoring the changes in tissue temperature comprises monitoring the tissue temperature at the focal region; and
    the method further comprises monitoring changes in tissue temperature along at least a portion of a propagation path of the ultrasound waves to the focal region using a strain-based approach.

5. The method of claim 1 wherein monitoring the changes in tissue temperature further comprises estimating the changes in tissue temperature using a strain-based approach that correlates changes in the sound speed of the detected echoes to changes in tissue temperature, wherein faster sound speeds correlate to higher temperatures.

6. The method of claim 5, further comprising:
    weighting the changes in tissue temperature estimated by the spectral-based approach according to a first coefficient;
    weighting the changes in tissue temperature estimated by the strain-based approach according to a second coefficient, wherein the second coefficient is different from the first coefficient; and
    combining the weighted changes in tissue temperature to form a temperature profile of the tissue.

7. The method of claim 1 wherein:
    propagating ultrasound waves into tissue comprises propagating high-intensity focused ultrasound (HIFU) waves toward a focal region in the tissue with a first array of first transducers, the first transducers comprising a piezocermaic material; and
    detecting echoes of the ultrasound waves comprises detecting the echoes with a second array of second transducers, the second transducers comprising a piezopolymer material.

8. The method of claim 1 wherein detecting echoes of the ultrasound waves comprises performing wavelet signal processing to enhance the resolution of the harmonics in the echoes.

9. The method of claim 1, further comprising modeling the tissue temperature as a three-dimensional temperature map.

10. A noninvasive temperature estimation system comprising:
    an ultrasound source configured to transmit ultrasound waves that become nonlinear at a focal region in tissue;
    means for detecting harmonics of the nonlinear waves; and
    means for determining changes in tissue temperature at the focal region in real-time using changes in the magnitude of at least one detected harmonic to estimate the tissue temperature, wherein a greater attenuation of an individual harmonic correlates to a greater increase in the tissue temperature.

11. The system of claim 10 wherein the ultrasound source comprises:
- a first array of first transducers, the first transducers comprising a first piezoelectric material configured to transmit nonlinear ultrasound waves; and
- a second array of second transducers different from the first transducers, the second transducers comprising a second piezoelectric material configured to detect up to at least a third harmonic of the ultrasound waves.

12. The system of claim 10 wherein the ultrasound source comprises a piezopolymer material.

13. The system of claim 10 wherein the ultrasound source is configured to detect harmonics of the nonlinear waves and the sound speed of reflected ultrasound waves, the detected harmonics and sound speeds being used to determine the tissue temperature.

* * * * *